(12) United States Patent
Telesca et al.

(10) Patent No.: US 6,875,444 B2
(45) Date of Patent: Apr. 5, 2005

(54) WRINKLE INDICATOR TAPE STRIP

(75) Inventors: Josephine Telesca, Trumbull, CT (US); Liam Anthony Murray, Monroe, CT (US); Robert Edward Gott, Norwalk, CT (US); Craig Stephen Slavtcheff, Guilford, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 542 days.

(21) Appl. No.: 10/022,458

(22) Filed: Oct. 29, 2001

(65) Prior Publication Data

US 2002/0182149 A1 Dec. 5, 2002

Related U.S. Application Data

(60) Provisional application No. 60/294,461, filed on May 30, 2001.

(51) Int. Cl.[7] .......................... A61F 13/00; A61K 9/00; A61L 15/16
(52) U.S. Cl. ....................... 424/443; 424/449; 424/448; 424/400
(58) Field of Search ................................ 424/443, 448, 424/449

(56) References Cited

U.S. PATENT DOCUMENTS

| | | |
|---|---|---|
| 3,571,947 A | 3/1971 | Maddison et al. |
| 3,906,933 A | 9/1975 | Tur et al. |
| 4,190,056 A | 2/1980 | Tapper et al. |
| 4,532,937 A | 8/1985 | Miller |
| 4,569,358 A | 2/1986 | Gormley |
| 4,981,145 A | 1/1991 | Goldstein |
| 5,088,502 A | 2/1992 | Miller |
| 5,094,248 A | 3/1992 | Kawam |
| 5,119,828 A | 6/1992 | Miller |
| 5,433,214 A | 7/1995 | Brehm et al. |
| 5,589,178 A | 12/1996 | Aubert et al. |
| 5,684,573 A | 11/1997 | Khazaka et al. |

(Continued)

FOREIGN PATENT DOCUMENTS

| | | |
|---|---|---|
| DD | 3725235 | 2/1989 |
| DE | 4337528 | 7/1995 |

(Continued)

OTHER PUBLICATIONS

Am J Dermatopathol 1987 Dec. 9(6):500–.
Elizabeth Arden "Challenge" Packaging—2000.

(Continued)

Primary Examiner—Thurman K. Page
Assistant Examiner—Isis Ghali
(74) Attorney, Agent, or Firm—Milton L. Honig

(57) ABSTRACT

A test kit and method for visualizing fine lines and wrinkles is provided, the kit including a transparent strip with an adhesive on one surface thereof and an imaging substrate with at least one darkened glossy area for receiving the transparent strip. Written instructions are provided in the kit. These advise a consumer to place the adhesive surface of the strip against a skin area requiring measurement. Thereafter the strip is removed and placed against the darkened area of the substrate. Topographical features of the skin can be viewed through the transparent strip with the transferred skin image onto the blackened background. A cosmetic anti-aging product can be applied to the skin over a period of time. Beneficial changes caused by the product are visualized through the test strip as periodic measurements are taken.

8 Claims, 1 Drawing Sheet

WEEK 0

WEEK 4

U.S. PATENT DOCUMENTS

| | | | |
|---|---|---|---|
| 5,727,949 | A | 3/1998 | Bar-Or et al. |
| 5,991,433 | A | 11/1999 | Osanai et al. |
| 6,270,783 | B1 * | 8/2001 | Slavtcheff et al. .......... 424/402 |
| 2001/0023327 | A1 | 9/2001 | Hill |
| 2003/0225345 | A1 * | 12/2003 | Slavtcheff et al. .......... 600/572 |

FOREIGN PATENT DOCUMENTS

| | | |
|---|---|---|
| FR | 2.063.743 | 6/1971 |
| FR | 2063743 | 6/1971 |
| FR | 2 821 541 | 3/2001 |
| GB | 2 284 154 | 5/1995 |
| JP | 2001275992 | 3/2000 |
| WO | 02/069802 | 9/2002 |

OTHER PUBLICATIONS

VICHY Laboratories Diagnostic Discs—1999.
Oil of Olay® D–SQUAME Test Discs—1999.
Dove® D–SQUAME Test Discs—1998.
reflect.com Test Discs—1999.
Soap & Cosmetics, May 2001, "Sampling Innovations" by Marie Tillery, Associate Editor, pp. 29–32.
Book Excerpt: Canadian Living, Mar. 2001.

* cited by examiner

WRINKLE INDICATOR TAPE STRIP

CROSS REFERENCES TO RELATED APPLICATIONS

This application claims benefit from Provisional Application Ser. No. 60/294,461, filed May 30, 2001.

BACKGROUND OF THE INVENTION

1. Field of the Invention

The invention concerns a test strip for evaluating changes in skin wrinkles, especially in the context of measuring the efficacy of anti-aging cosmetic products.

2. The Related Art

A number of publications have disclosed test devices for the lay person to self-diagnose their skin conditions. U.S. Pat. No. 3,571,947 (Maddison et al.) discloses a system for identifying blemishes. A flexible, compliant film of plastic is imprinted with pictorials of various types of common blemishes. These reflect different dermal diseases. They are cross-referenced with a handbook identifying the diseases from the type of blemish. Cross-indexing treatments further provides a suggested treatment to remedy the medical condition.

U.S. Pat. No. 5,727,949 (Bar-Or et al.) provides a dual ring panel reference card. The panels are mounted for relative movement whereby a selected diagnostic characteristic of a skin problem can be aligned with a second diagnostic characteristic and a determinable prognosis revealed from the specific paired characteristics.

CuDerm Corporation has developed a simple diagnostic test to determine the degree of skin dryness. CuDerm utilizes adhesive discs (D-SQUAME) capable of removing a small section of squameous cells (skin cells) and compares the results against a chart. The disc is a transparent plastic with adhesive on one side. The test involves placing the adhesive surface of the disc against a user's cheek, peeling off the disc and placing same on a dark background card. Flakes from the skin stick to the adhesive surface and are visualized against the dark background. Other than loose flakes, no topographical imprint is ever taken from the evaluated user's skin.

There are many cosmetic products sold which advertise certain skin benefits. Consumers usually cannot easily discern whether the claimed benefit is actually delivered. Even if perceivable, these actives impart an effect which may emerge only slowly over a period of time. Anti-aging actives are particularly illustrative. Facial fine lines and wrinkles can be minimized with actives such as alpha hydroxycarboxlic acids and/or retinol, to provide some visible improvement over an extended application period. They don't function instantaneously.

Accordingly, it is an object of the present invention to provide a low-cost simple test for a consumer to self-evaluate a cosmetic product's anti-aging benefits over a prolonged application period.

Another object of the present invention is to provide a low-cost simple self-evaluation tool for measuring changes in fine lines and wrinkles on the face or other aging susceptible parts of the human dermis.

SUMMARY OF THE INVENTION

A test kit for visualizing fine lines and wrinkles on a person's skin is provided which includes:

(i) a transparent strip provided with an adhesive on one surface thereof, the adhesive having sufficient tack to maintain an imprint of fine lines and wrinkles after removal of the strip from the skin;

(ii) an imaging substrate with at least one darkened area for receiving the transparent strip; and (iii) written instructions within the kit directing a consumer to place the adhesive surface of the strip against a skin area requiring measurement, to remove the strip and place same against the darkened area of the substrate, to repeat the aforesaid procedure at a future time followed by comparison of patterns resultant from the first and second strip applications to the skin.

Further, there is provided a method for evaluating efficacy of an anti-aging cosmetic product, the method including:

(A) providing a kit which includes:
 (i) a transparent strip provided with an adhesive on one surface thereof, the adhesive having sufficient tack to maintain an imprint of fine lines and wrinkles after removal of the strip from the skin; and
 (ii) an imaging substrate with at least one darkened area for receiving the transparent strip;

(B) applying the cosmetic product to the skin;

(C) placing the adhesive surface of the strip against the skin treated with the cosmetic product in step (B);

(D) removing the strip and placing same against one of the at least darkened areas of the substrate; and (E) repeating steps (C) and (D) at a future time followed by comparison of patterns resultant from the first and second strip applications to the skin.

BRIEF DESCRIPTION OF THE DRAWING

Additional objects, features and benefits of the present invention will become more readily apparent from consideration of the drawing in which.

DETAILED DESCRIPTION OF THE INVENTION

Now there has been found a simple diagnostic test for allowing a consumer to evaluate the claimed effectiveness of anti-aging cosmetic products. Effectiveness of the anti-aging result can be monitored over a period of time through an inexpensive kit. The kit employs a transparent plastic strip coated with a transparent adhesive layer. When applied to a wrinkle prone area of the face or body, the adhesive layer accepts a topological wrinkle imprint. Removal of the strip from this wrinkle area can then be imaged by placement onto a darkened, preferably black field.

Figure 1:
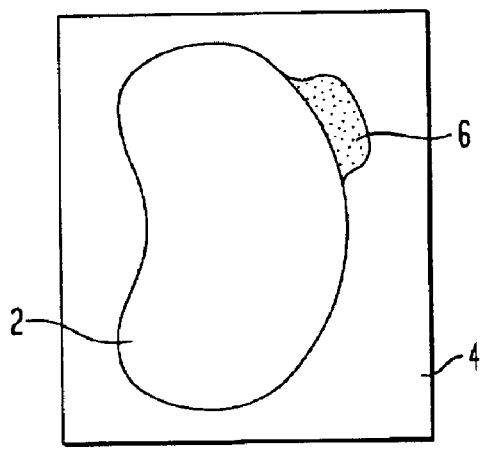
FIG. 1 is a first embodiment of an application strip according to the present invention.

FIG. 1 illustrates a transparent strip 2 adhesively attached to a release backing 4. Strip 2 is kidney-shaped for placement adjacent either the right or left eye so as to cover the periorbital canphus (crow's foot area). This curvilinear shape allows for maximum coverage around an outer corner of the eye.

A tab 6 is attached to the strip 2. The tab serves as a gripping structure. Separation of the strip from the release backing is facilitated by initiating removal at the tab. The opaque, preferably black coloration of the tab in contrast to the transparency of the strip signals to a user the difference of this area and cues the user to start lifting at that point.

Figure 2:
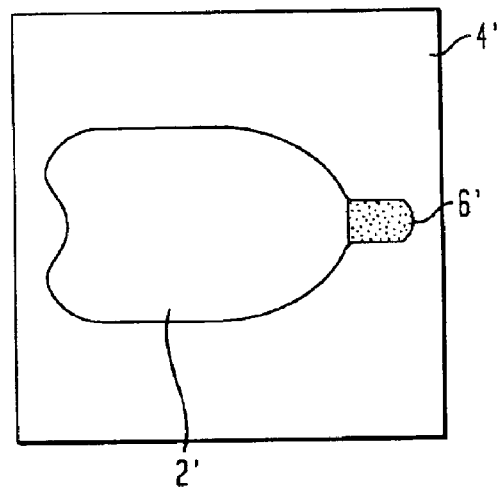
FIG. 2 is a second embodiment of an application strip according to the present invention.

FIG. 2 illustrates a second embodiment of a more elongate double lobed shape. Strip 2' is removably adhered onto a release backing 4'. Tab 6' is oriented between both lobes of the strip and lies along an axis of symmetry bisecting the strip. The elongate nature of this embodiment even more than the first embodiment ensures that eyebrow hairs are not trapped under the adhesive when applied. It is undesirable to capture hairs. Any hairs caught in the adhesive may cause pain upon the strip being removed. This, is considered an undesirable ouch factor.

Figure 3:
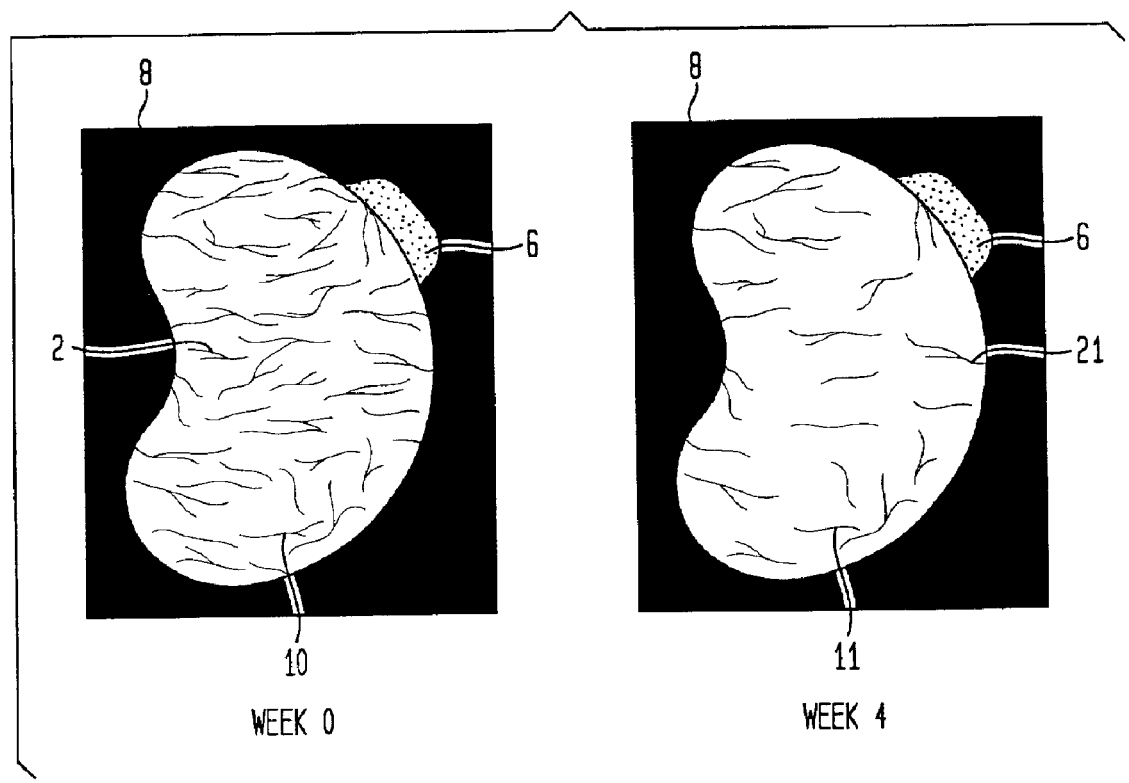
FIG. 3 is the application strip of the embodiment shown in FIG. 1 subsequent to being placed on the skin, removed therefrom and mounted on a darkened field reading card.

In the procedure for testing efficacy of various anti-aging products, the strip is removed from its release backing. Thereupon it is placed along an area of skin to be imaged for its topography. Facial areas are primarily intended for evaluation, and more particularly areas surrounding the eye. Subsequently, the strip is removed and placed upon an imaging card 8. The dark, preferably black background of the card fixes the imprint while the transparent strip allows a view of that imprint. FIG. 3 illustrates the strip showing fine lines and wrinkles 10 being visualized against the black background of the imaging card.

Subsequent to a baseline analysis of fine lines and wrinkles, treatment is begun with a selected cosmetic anti-aging product. Treatment is continued for a period of time sufficient to allow the product to treat the signs of aging.

A second imaging field is placed adjacent to the first. After the treatment period of time, such as four weeks, another imprint is taken by a second transparent strip 21. If the cosmetic product is properly functioning, fewer fine lines and wrinkles 11 will appear on the imaged second field. This procedure can then be repeated at six or eight weeks or at any further time interval. Each test will employ a fresh strip and new blackened area on the same or another image card.

In a preferred embodiment, the kit includes a dusting device. Most preferred is a dusting paper which is formed of a cellulosic substrate supporting a water-dispersible titanium dioxide embedded therein. This device is available from Leading Plus International, Taiwan. Prior to applying the adhesive transparent strip, the target area of the face is rubbed with the dusting paper. Powdered titanium dioxide is deposited thereon as an even film. Contact subsequently with the adhesive strip allows the latter to preferentially adhere to powder deposit along ridges of the fine lines and wrinkles. An image in powder form of those fine lines and wrinkles is thereby obtained. Although a paper delivery system as described above is preferred, dusting powder can also be delivered from a shaker container similar to those for the dispensing of talcum powder.

Strips for use in the present invention will be transparent articles allowing observation of any patterns on a lower surface thereof. Suitable materials for the strip are plastics or cellulosics of any variety which can be formed as transparent films. Typically the plastic may be selected from polyethylene, polypropylene, polystyrene, polyester, polycarbonate, polyacrylate, polyvinyl chloride, polyvinyl alcohol and polybutene. Not only homopolymers but copolymers may be utilized for the strip material. Copolymers may be formed from such monomers as $C_2$–$C_{10}$ olefins, vinyl chloride, acrylates and styrene constructed through free-radical polymerization. Condensation plastics may also be utilized in the formation of copolymers wherein the monomers may be selected from $C_2$–$C_{10}$ dicarboxylic acids, $C_2$–$C_{10}$ polyols, $C_2$–$C_6$ alkoxylates and combinations thereof. Polyethylene, polypropylene and polyester terephthalate are the preferred plastic substrates for forming the strip.

The thickness of the strip may range anywhere from about 0.001 to about 2 mm, preferably from about 0.01 to about 1 mm, more preferably from about 0.1 to about 0.5 mm and optimally from about 0.5 to about 0.8 mm.

The backing is typically made from a material and in a manner that is generally impervious to the adhesive. The backing may be elastic or non-elastic but preferably the former. Flexibility allows easier removal of the adhesive strip. The backing can be formed from a variety of materials including organic polymers and cellulosics. A release coating such as a silicone may be placed on an upper surface of the backing to ease removal of the adjacent adhesive strip.

The adhesive will be a pressure sensitive type preferably as a layer with an average thickness from about 0.01 mm to about 3 mm, preferably from about 0.05 mm to about 2 mm, more preferably from about 0.1 mm to about 1 mm, optimally from about 0.4 mm to about 0.8 mm.

Pressure sensitive adhesives suitable for use in this invention are coatable adhesives. A wide variety of coatable pressure sensitive adhesives can be used, such as solvent coatable, hot melt coatable, as well as latex PSA's that are coatable out of water. Also, solventless curable adhesives (often referred to as 100% solids) can be used. Where thicker adhesive coatings are desired, it may be desirable either to apply multiple layers of the adhesive, hot melt coat, or to photopolymerize the adhesive in situ. Specific examples of pressure sensitive adhesives include acrylates, such as isooctyl acrylate/acrylic acid copolymers, tackified acrylates, and plasticizer-containing acrylates such as those disclosed in U.S. Pat. No. 4,946,742 (Landin); natural or synthetic rubber resins, including thermoset rubbers as well as thermoplastic rubbers and elastomers, such as nitrile rubbers (e.g., acrylonitrile-butadiene), styrene-butadiene, styrene-isoprene, styrene-butadiene-styrene, styrene-isoprene-styrene, and natural rubber; silicone-based adhesives, such as polysiloxanes; polyolefins; polyesters; polyamides; and polyurethanes.

Particularly preferred are the acrylic type pressure sensitive adhesives. Most especially a pressure sensitive adhesive with a low tack value. These materials are commercially available under the FLEXCON.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All parts, percentages and proportions referred to herein and in the appended claims are by weight unless otherwise illustrated.

The foregoing description and examples illustrate selected embodiments of the present invention. In light thereof variations and modifications will be suggested to one skilled in the art, all of which are within the spirit and purview of this invention.

What is claimed is:

1. A test kit for visualizing fine lines and wrinkles on a person's skin comprising:
    (i) a transparent first strip provided with an adhesive on one surface thereof, the adhesive having sufficient tack to maintain an imprint of fine lines and wrinkles after removal of the strip from the skin;

(ii) an imaging substrate with at least one darkened area for receiving the transparent strip; and (iii) a dusting powder for application against the skin prior to placement thereon of the adhesive surface of the strip; and (iv) written instructions within the kit directing a consumer to place the dusting powder against the skin and thereon to place the adhesive surface of the strip against a skin area requiring measurement, to remove the strip and place same against the darkened area of the substrate, to repeat the aforesaid procedure at a future time with a second strip followed by comparison of patterns resultant from the first and second strip applications to the skin.

2. The kit according to claim 1 wherein the adhesive is a pressure sensitive adhesive.

3. The kit according to claim 2 wherein the adhesive is an acrylate polymer.

4. A method for evaluating efficacy of an anti-aging cosmetic product, the method comprising:

(A) providing a kit which comprises:
(i) a transparent first strip provided with an adhesive on one surface thereof, the adhesive having sufficient tack to maintain an imprint of fine lines and wrinkles after removal of the strip from the skin;
(ii) a dusting powder; and
(iii) an imaging substrate with at least one darkened area for receiving the transparent strip;

(B) applying the cosmetic product to the skin;

(C) placing the dusting powder against the skin treated with the cosmetic product in step (B);

(D) placing the adhesive surface of the strip against the skin treated with the dusting powder and the cosmetic product;

(E) removing the strip and placing same against one of the at least darkened areas of the substrate; and (F) repeating steps (D) and (E) at a future time with a second strip followed by comparison of patterns resultant from the first and second strip applications to the skin.

5. The method according to claim 4 wherein the dusting powder is carried to the skin on a paper.

6. The method according to claim 4 wherein the dusting powder is a water-dispersible titanium dioxide.

7. The kit according to claim 1 wherein the dusting powder is carried to the skin on a paper.

8. The kit according to claim 1 wherein the dusting powder is a water-dispersible titanium dioxide.

* * * * *